United States Patent [19]

Riesser

[11] 4,144,197
[45] Mar. 13, 1979

[54] DEHYDROGENATION CATALYST

[75] Inventor: Gregor H. Riesser, Houston, Tex.

[73] Assignee: Shell Oil Company, Houston, Tex.

[21] Appl. No.: 899,055

[22] Filed: Apr. 24, 1978

Related U.S. Application Data

[63] Continuation-in-part of Ser. No. 787,646, Apr. 14, 1977, abandoned.

[51] Int. Cl.² .................. B01J 23/10; B01J 23/78; B01J 23/84; B01J 23/88
[52] U.S. Cl. .................................. 252/462; 260/669 R
[58] Field of Search ..................... 252/462; 260/669 R

[56] References Cited

U.S. PATENT DOCUMENTS

| 3,179,707 | 4/1965 | Lee | 260/669 R |
| 3,904,552 | 9/1975 | O'Hara | 252/458 |

*Primary Examiner*—W. J. Shine

[57] ABSTRACT

Addition of oxidic compounds of molybdenum and/or tungsten, cerium and optionally cobalt and/or chromium to iron-potassium-vanadium oxide catalysts useful in the dehydrogenation of hydrocarbons to the corresponding more unsaturated hydrocarbons results in an improved catalyst.

11 Claims, No Drawings

DEHYDROGENATION CATALYST

This application is a continuation-in-part of copending application Ser. No. 787,646, filed Apr. 14, 1977, now abandoned.

BACKGROUND OF THE INVENTION

1. Field of the Invention

This invention relates to improved catalysts for the dehydrogenation of hydrocarbons to corresponding more-unsaturated hydrocarbons, more particularly, to the production of vinyl aromatic hydrocarbons from alkyl aromatic hydrocarbons and to the production of olefins from the corresponding more-saturated aliphatic hydrocarbons.

2. The Prior Art

The vinyl benzenes and butadienes play a particularly important role in the preparation of synthetic rubbers, plastics and resins. The polymerization of styrene for example with various co-monomers such as butadiene to produce synthetic rubbers is well known as is the polymerization of styrene to produce polystyrene resins.

Styrene and butadiene are typically produced from ethyl benzene and butylene, respectively, by dehydrogenation over solid catalysts in the presence of steam, and at temperatures ranging from 500° C. to 700° C. The class of catalysts found to be the most effective for this process is a potassium oxide (carbonate) promoted, chromium oxide stabilized, iron oxide material. Considerable research has gone into attempting to improve the activity and selectivity of this class of catalysts. Any improvement which results in either increasing the selectivity (moles of desired product produced per mole of reactant reacted) or the conversion (moles of reactant reacted per mole of starting material) without lowering the other is economically attractive since the result is that the yield (moles of desired product produced per mole of reactant) of the product has been increased. Any increase in the numerical value of the yield results in a more efficient operation with more reactant being converted into the desired product. In commercial operations, many of which produce millions of pounds of product per year, a trade-off is frequently effected between selectivity and conversion. An increase of only 1 or 2 percentage points in the selectivity can result in a substantial savings of starting materials. An increase in conversion can substantially reduce capital expenditure and energy consumption. The trade-off may vary depending on raw materials costs, energy costs, and the age of the plant.

The addition of vanadium pentoxide is known to improve the selectivity of the iron-chromium-potassium oxide catalysts. Such catalysts containing vanadium pentoxide were disclosed in U.S. Pat. No. 3,361,683 to W. R. Gutmann, issued Jan. 2, 1968, in U.S. Pat. No. 3,084,125 to F. J. Soderquist issued Apr. 2, 1963, or in Belgium Pat. No. 828,252, published Oct. 23, 1975.

Addition of cobalt to a typical iron-chromium-potassium oxide catalyst has been disclosed in U.S. Pat. No. 3,291,756 to R. S. Bowman, issued Dec. 13, 1966. Copending applications Ser. Nos. 740,272, now U.S. Pat. No. 4,052,338, and 740,264, now abandoned, filed Nov. 8, 1976 disclose the addition of small amounts of cobalt to iron-chromium-potassium-vanadium oxide catalysts. Copending Ser. No. 763,180 filed Jan. 27, 1977, now U.S. Pat. No. 4,098,723, discloses the addition of small amounts of cobalt to iron-potassium-vanadium oxide catalyst. U.S. Pat. No. 3,904,552 to O'Hara, issued Sept. 9, 1975, disclosed the use of cerium and molybdenum in dehydrogenation catalysts. Belgium Pat. No. 811,145 published June 17, 1974 disclosed the use of cerium in dehydrogenation catalysts. Belgium Pat. No. 811,191, published June 17, 1974 disclosed the use of cerium and molybdenum in dehydrogenation catalysts. U.S. Pat. No. 3,703,593 to Turley et al issued Nov. 21, 1972, disclosed the use of molybdenum as a promoter. U.S. Pat. No. 3,179,707 to Lee, issued Apr. 20, 1965, disclosed the use of vanadium, cobalt, cerium, and other metal in dehydrogenation catalysts. U.S. Pat. No. 3,505,422 issued Apr. 7, 1970 to Brewer et al and U.S. Pat. No. 3,424,808 issued Jan. 28, 1969 to Brewer et al disclosed the use of Group VIII metals, particularly cobalt, among others, in dehydrogenation catalysts. U.S. Pat. No. 3,223,743 issued Dec. 14, 1965 to Alistair disclosed the use of group IV to VIII metals particularly cerium in dehydrogenation catalysts. U.S. Pat. No. 2,603,610 to Amos et al, issued July 15, 1952; U.S. Pat. No. 2,414,585 to Eggertsen et al, issued Jan. 21, 1947; U.S. Pat. No. 2,460,811 to Davies et al, issued Feb. 8, 1949 and U.S. Pat. No. 2,461,147 to Davies et al, issued Feb. 8, 1949 are references that disclosed a number of metals used in dehydrogenation catalysts.

STATEMENT OF INVENTION

It has now been found that when compounds of molybdenum and/or tungsten, cerium and optionally cobalt and/or chromium are added to dehydrogenation catalysts comprising iron oxide, vanadium oxide and potassium oxide/carbonate, the selectivity and/or conversion to unsaturated hydrocarbons from corresponding more-saturated materials is improved. In particular, yield to styrene from ethylbenzene and butadiene from butylene is improved. In particular, the catalysts of this invention are useful for the production of olefins from the corresponding more-saturated aliphatic hydrocarbons, and specifically for the production of butadiene from butylene or isoprene from amylene. The catalyst of this invention is further of use in producing alkenyl aromatic hydrocarbons from alkyl aromatic hydrocarbons particularly lower alkenyl aromatic hydrocarbons from lower alkyl aromatic hydrocarbons as for example, ethyl benzene, isopropylbenzene, diethylbenzene and ethyl methyl benzene, where the lower alkenyl and lower alkyl groups have from two to six carbon atoms, and specifically is useful for the production of styrene from ethyl benzene. These catalysts are also auto-regenerative under conditions at which the dehydrogenation reaction is effected, that is, they are capable of being continually regenerated under the conditions of the reaction.

DETAILED DESCRIPTION OF THE INVENTION

The catalysts of this invention typically contain (a) from about 20 to about 95 and preferably from about 25 to about 90 percent by weight of iron compound, measured as ferric oxide, (b) from about 3 to about 30 and preferably from about 5 to about 25 percent by weight of a potassium compound, measured as potassium oxide, (c) from about 0.01 to about 9, preferably from about 0.1 to about 9, more preferably from about 0.1 to about 6 percent by weight of a vanadium compound measured as vanadium pentoxide, (d) from 0.01 to about 20, preferably from about 0.1 to about 20, more preferably from about 0.1 to about 15, even more preferably from about 0.2 to about 10, and most preferably from about 0.3 to about 10 percent by weight of a molybdenum and/or tungsten compound, measured as molybdenum trioxide and/or tungsten trioxide, (e) from about 0.01 to about 50 preferably from about 0.1 to about 30, more preferably from about 0.1 to about 20, even more preferably from about 0.3 to about 20, and most preferably from about 0.5 to about 15 percent by weight of a cerium compound measured as cerous oxide ($Ce_2O_3$), (f) optionally containing up to about 50 (i.e., from 0 to about 50), more preferably up to about 40 (i.e. from 0 to about 40) and most preferably up to about 30 (i.e., from 0 to about 30) percent by weight of a cobalt compound, measured as cobaltous oxide, and (g) optionally containing up to about 30 (i.e., from 0 to about 30) and preferably up to about 20 (i.e., from about 0 to about 20) percent by weight of a chromium compound measured as chromic oxide ($Cr_2O_3$). Alternately stated, these catalysts contain (a) from about 14 to about 67 and preferably from about 17 to about 63 percent by weight of iron oxide, measured as iron metal, (b) from about 2 to about 25 and preferably from about 4 to about 21 percent by weight of a potassium oxide measured as potassium metal, (c) from about 0.005 to about 5 preferably from about 0.05 to about 5, more preferably from about 0.05 to about 4 percent by weight of a vanadium oxide measured as vanadium metal, (d) from 0.006 to about 16, preferably from about 0.06 to about 16, more preferably from about 0.06 to about 12, even more preferably from about 0.1 to about 8, and most preferably from about 0.2 to about 8 percent by weight of a molybdenum and/or tungsten oxide, measured as molybdenum metal and/or tungsten metal, (e) from about 0.008 to about 43 preferably from about 0.08 to about 26, more preferably from about 0.08 to about 17, even more preferably from about 0.2 to about 17, and most preferably from about 0.4 to about 13 percent by weight of a cerium oxide measured as cerous metal, (f) optionally containing up to about 40 (i.e., from 0 to about 40), more preferably up to about 32 (i.e. from 0 to about 32) and most preferably up to about 25 (i.e., from 0 to about 24) percent by weight of a cobalt oxide, measured as cobaltous metal, and (g) optionally containing up to about 21 (i.e., from 0 to about 21) and preferably up to about 14 (i.e., from about 0 to about 14) percent by weight of a chromium oxide measured as chromium metal.

Variances within the general composition described above depend in part on whether the catalyst is used to produce vinyl aromatic compounds or olefinic compounds.

Catalysts for the production of vinyl aromatic compounds such as styrene from ethyl benzene and alpha-methylstyrene from cumene typically contain from about 35 to about 95 and preferably from about 40 to about 90 percent by weight of iron compound measured as ferric oxide; from about 5 to about 20 and preferably from about 6 to about 15 percent by weight of potassium compound measured as potassium oxide; from about 0.01 to about 9, more preferably from about 0.1 to about 9 and most preferably from about 0.2 to about 6 percent by weight of a vanadium compound measured as vanadium pentoxide; from about 0.01 to about 20, preferably from about 0.1 to about 20, more preferably from about 0.1 to about 15, even more preferably from about 0.2 to about 10 and most preferably from about 0.3 to about 10 percent by weight of a molybdenum and/or tungsten measured as molybdenum trioxide and/or tungsten trioxide; from about 0.01 to about 50, preferably from about 0.1 to about 30, more preferably from about 0.1 to about 20, even more preferably from about 0.3 to about 20, and most preferably from about 0.5 to about 15 percent by weight of a cerium compound measured as cerous oxide; optionally up to about 50, preferably up to about 40, and most preferably up to about 30 percent by weight of a cobalt compound measured as cobaltous oxide; and optionally up to about 30, preferably up to about 20 percent by weight of a chromium compound measured as chromic oxide. Alternately stated, these catalysts contain from about 24 to about 67 and preferably from about 27 to about 63 percent by weight of iron oxide measured as iron metal; from about 4 to about 17 and preferably from about 5 to about 13 percent by weight of potassium oxide measured as potassium metal; from about 0.005 to about 5, more preferably from about 0.05 to about 5 and most preferably from about 0.1 to about 4 percent by weight of a vanadium oxide measured as vanadium metal; from about 0.006 to about 16, preferably from about 0.06 to about 16, more preferably from about 0.06 to about 12, even more preferably from about 0.1 to about 8 and most preferably from about 0.2 to about 8 percent by weight of a molybdenum and/or tungsten oxide measured as molybdenum metal and/or tungsten metal; from about 0.008 to about 43, preferably from about 0.08 to about 26, more preferably from about 0.08 to about 17, even more preferably from about 0.2 to about 17, and most preferably from about 0.4 to about 13 percent by weight of a cerium oxide measured as cerium metal; optionally up to about 40 preferably up to about 32, and most preferably up to about 24 percent by weight of a cobalt oxide measured as cobalt metal; and optionally up to about 21, preferably up to about 14 percent by weight of a chromium oxide measured as chromium metal.

Catalyst for the production of dienes from mono-olefins such as, for example, isoprene from amylene or butadiene from butylene typically contain from about 30 to about 75 and preferably from about 35 to about 70 percent by weight of iron compound measured as ferric oxide, from about 15 to about 30 and preferably from about 20 to about 30 percent by weight of potassium compound measured as potassium oxide; from about 0.01 to about 9, more preferably from about 0.1 to about 9, and most preferably from about 0.2 to about 6 percent by weight of a vanadium compound measured as vanadium pentoxide; from about 0.01 to about 20, preferably from about 0.1 to about 20, more preferably from about 0.1 to about 15, even more preferably from about 0.2 to about 10, and most preferably from about 0.3 to about 10 percent by weight of a molybdenum and/or tungsten compound measured as molybdenum trioxide and/or tungsten trioxide; from about 0.01 to about 50, preferably from about 0.1 to about 30, more preferably from about 0.1 to about 20, even more preferably from about 0.3 to about 20, and most preferably from about 0.5 to about 15 percent by weight of a cerium compound measured as cerious oxide; optionally up to about 50, preferably up to about 40, and most preferably up to about 30 percent by weight of a cobalt compound measured as cobaltous oxide; and optionally up to about 30, preferably up to about 20 percent by weight of a chromium compound measured as chromic oxide. Alternately stated, these catalysts contain from about 21 to about 53 and preferably from about 24 to about 49 percent by weight of iron oxide measured as iron metal; from about 12 to about 25 and preferably from about 16 to about 25 percent by weight of potassium oxide measured as potassium metal; from about 0.005 to about 5, more preferably from about 0.05 to about 5, and most preferably from about 0.1 to about 4 percent by weight of a vanadium oxide measured as vanadium metal; from about 0.006 to about 16, preferably from about 0.06 to about 16, more preferably from about 0.06 to about 12, even more preferably from about 0.1 to about 8, and most preferably from about 0.2 to about 8 percent by weight of a molybdenum and/or tungsten oxide measured as molybdenum metal and/or tungsten metal; from about 0.008 to about 43, preferably from about 0.08 to about 26, more preferably from about 0.08 to about 17, even more preferably from about 0.2 to about 17, and most preferably from about 0.4 to about 13 percent by weight of a cerium oxide measured as cerium metal; optionally up to about 40, preferably up to about 32, and most preferably up to about 24 percent by weight of a cobalt oxide measured as cobalt metal; and optionally up to about 21, preferably up to about 14 percent by weight of a chromium oxide measured as chromium metal.

It is known that the most selective catalysts are those having surface areas below 10 sq. meter per gram, and in many cases below 5 sq. meter/gram. If iron oxides have surface areas in excess of this requirement, the surface area can be reduced by precalcining the iron oxides at temperatures exceeding 700° C. for a period of time ranging from one-half hour to several hours.

The strength of the catalysts can be improved by adding binding agents such as calcium aluminate and Portland cement. However, catalyst strength can also be improved by calcining the extruded pellets at temperatures ranging from about 700° C. to about 1000° C. Calcination at these temperatures can alleviate the use of binding agents.

While most of the above methods result in catalysts having desired surface area, they also result in catalysts having a relatively high density. It has been found that catalysts having a highly porous structure and a low surface area are highly active in catalytic dehydrogenation. Various methods have been employed to form highly porous catalysts. For example, combustible materials, such as sawdust, carbon, wood flour, etc., have been added during catalyst formation, and then burned out after the pellet has been formed. Many of these porosity-promoting aids also assist in facilitating extrusion of pellets, for example, the use of graphite and aqueous solutions of methyl cellulose.

Many forms of iron oxide can be used in preparation of the catalyst of this invention. Typically, iron oxides employed in catalyst preparations of this sort are usually a synthetically produced, powdered red, red-brown, yellow or black pigment. The red or red-brown pigments are highly pure ferric oxide, while the black pigment is the magnetic form, ferrosoferric oxide ($Fe_3O_4$), which is usually found in the catalyst under various reaction conditions. The yellow iron oxides consist of the monohydrated form of ferric oxide. These oxides are prepared by various methods, e.g., oxidation of iron compounds, roasting, precipitation, calcination, etc. A suitable form of iron compound is the monohydrated yellow iron oxide used in the preparation of catalysts according to U.S. Pat. No. 3,360,597, issued Dec. 26, 1967, and U.S. Pat. No. 3,364,277, issued Jan. 16, 1968. Particularly suitable are pigment grade red iron oxides of purities exceeding 98% wt. These red oxides have surface areas ranging from 2 to 50 $m^2$/gram and particle sizes from 0.1 to 2 microns. The iron compound is present in the catalyst in either one or a mixture of both of its possible oxidation, states, i.e., as ferrous iron or ferric iron or mixtures thereof, as for example, ferrosoferric iron. The iron compound present is conveniently measured as ferric oxide.

The potassium promoter is added to the catalyst in various forms. For example, it may be added as the oxide, or as other compounds which are convertible, at least in part, under calcination conditions, to the oxides, such as the hydroxides, the carbonates, the bicarbonates, the phosphates, the borates, the acetates, and the like. Preferred potassium compounds are potassium oxide and potassium carbonate, particularly potassium carbonate. The potassium compound is present in the catalyst as a potassium oxide, a potassium carbonate or a mixture thereof. High carbon dioxide partial pressures in the reaction gases will favor higher carbonate to oxide ratios and vice versa. The potassium compound(s) is conveniently measured as potassium oxide.

Vanadium is added to the catalyst as vanadium pentoxide or as salts or other compounds thermally decomposable to the oxides, such as sulfates, oxysulfates, sulfides, or vanadates. The vanadium is present in the catalyst in one or mixtures of more than one of its possible oxidation states, the pentavalent state being the preferred state. The vanadium compound(s) is conveniently measured as the vanadium pentoxide.

A heavy metal selected from the group consisting of molybdenum, tungsten or mixtures thereof is added to the catalyst as molybdenum and/or tungsten trioxide or as salts or other compounds thermally decomposable to the oxide, such as hydroxides, bromides, chlorides and the like. The molybdenum and/or tungsten is present in the catalyst in one or mixtures of more than one of its possible oxidation states, the hexavalent state being the preferred state. The heavy metal compound(s) is conveniently measured as the heavy metal trioxide.

Cerium is added to the catalyst in various forms. For example, it may be added as the oxide, or as other compounds which are convertible, at least in part, under calcination conditions, to the oxides, such as the hydroxide, the carbonates, the bicarbonates, the oxalates and the like. Preferred cerium compounds are cerium oxide and cerium carbonate, particularly cerium carbonate. The cerium compound is present in the catalyst in either the ceric oxidation state, the cerous oxidation state, or a mixture of both oxidation states (ceric preferred). The cerium compound is conveniently measured as cerous oxide ($Ce_2O_3$).

Cobalt has been found to be beneficial when added to vanadium promoted iron-chromium-potassium and iron-potassium catalysts as disclosed in copending application Ser. Nos. 740,262 and 740,264 filed Nov. 8, 1976 and Ser. No. 763,180, filed Jan. 27, 1977. Addition of cobalt to the catalysts of this invention can provide a slight improvement in activity and when this activity is desired, the cobalt is added to the catalyst as the oxide, or as compounds decomposable to the oxide such as hydroxides, carbonates, bicarbonates, nitrates, acetates, oxalates, and the like. The cobalt is present in the catalyst in the cobaltous or cobaltic oxidation state or mixtures thereof. The cobalt compound(s) is conveniently measured as the cobaltous oxide.

Other oxides such as these disclosed in copending application Ser. No. 787,647, filed Mar. 14, 1977, now abandoned, can also be added.

Chromium oxide has been typically added to alkali-promoted iron oxide catalysts to extend their life. Environmental and toxicity considerations may militate against the use of chromium compounds in favor of somewhat shorter catalyst life under certain conditions. However, chromium, when optionally used in the catalyst of this invention is added to the catalyst in the form of a chromium oxide or in the form of chromium compounds which decompose upon calcination to the oxides, as for example chromium nitrates, hydroxides, acetates, and the like.

The catalyst of this invention will consist of mixtures of oxides, both simple oxides such as ferric oxide and complex oxides such as the spinels and ferrites as well as oxides such as vanadates, etc., and carbonates, with carbonates of potassium preferred. Specific oxides present in the calcined catalyst will be determined by calcining conditions, reaction conditions, etc. Typically calcining conditions range from about 500° C. to about 1100° C. Since typical commercial dehydrogenation reactions are carried out in the presence of steam and carbon dioxide, the catalyst contains a proportion of carbonates and some hydroxides. The catalyst of this invention comprises a mixture of oxides and carbonates having from about 20 to about 95 percent by weight of an iron oxide, measured as ferric oxide; from about 3 to about 30 percent by weight of a potassium compound selected from the group consisting of a potassium oxide, a potassium carbonate, or mixtures thereof, measured as potassium oxide; from about 0.01 to about 9 percent by weight of a vanadium oxide, measured as vanadium pentoxide; from about 0.01 to about 20 percent by weight of a molybdenum and/or tungsten oxide, measured as molybdenum and/or tungsten trioxide; from about 0.01 to about 50 percent by weight of a cerium oxide, measured as cerous oxide; optionally up to about 50 percent by weight of a cobalt oxide, measured as cobaltous oxide; and optionally up to about 30 percent by weight of a chromium oxide, measured as chromic oxide.

The catalyst of this invention is compounded in a variety of ways. One method is to ballmill together a mixture of the desired oxides, adding a small amount of water, and extruding the paste formed to produce small pellets, which are then dried and calcined at temperatures above 500° C. Another method is to dissolve the components together, spray dry these components for form a resulting powder, calcine the powder into the resultant oxides, and then add sufficient water to form a paste and extrude into pellets, dry and calcine. Another procedure would involve precipitating those materials which are precipitatable, such as iron, as the resultant hydroxides, partially de-watering the resultant precipitate, adding soluble salts of potassium and vanadium, and then subsequently extruding, drying and calcining the resultant pellets. A pelleting mill could also be used to form the pellets. A preferred method is to dry-blend powders of iron oxide, molybdenum and/or tungsten trioxide, cerium carbonate, cobalt carbonate and vanadium pentoxide, and potassium carbonate, add water, optionally containing potassium carbonate in solution, and then mull and pelletize the mixture, subsequently substantially drying at a temperature from about 50° C. to about 300° C. and then calcining the pellets at a temperature ranging from about 600° C. to about 1000° C. to form the final product. Alternatively, the vanadium pentoxide is dissolved in the potassium carbonate solution, rather than dry-mixed with the iron oxide, molybdenum and/or tungsten oxide, cerium carbonate and cobalt carbonate. An alternate process for preparing the catalyst is where iron, potassium, vanadium and molybdenum, cerium and optionally chromium and cobalt compounds are combined with water to form a paste, the paste mulled and formed into pellets, substantially all the water is removed from the pellets in a drying step and the pellets are calcined at a temperature ranging from about 600° C. to 1000° C. The drying and calcining steps can be combined into one sequential step still within the scope of this invention in a furnace whose temperature is suitably programmable such as by varying the heat input or the residence time of the pellets through the furnace.

The optimum size of the pellets produced will vary according to the need of various processes. Catalyst pellets having a diameter of from ⅛ to ⅜ of an inch, and from ⅛ to ⅝ of an inch in length are typical. The smaller diameter catalysts are generally more active but provide increased pressure drops.

The dehydrogenation reaction is usually carried out at reaction temperatures of about 500°–700° C. However, higher or lower temperatures may be used without departing from the scope of this invention. The use of atmospheric, sub-atmospheric, or super-atmospheric pressure is suitable. However, it is preferable to operate at as low a pressure as is feasible, and atmospheric or subatmospheric pressure is preferred. The process of the invention may be carried out in batch, semi-continuous, or continuous operation, with continuous operation being preferred. The catalyst is employed in the form of a fixed bed, or in fluidized or suspended form. It is preferable to utilize a fixed bed. The reaction may be carried out in single stage reactors or by staging in series reactors. The reactors may be of various designs, e.g., downflow reactors, radial reactors, etc.

With the use of the catalyst of this invention, it is desirable to add steam to the reactant feed to aid in the removal of carbonaceous residues from the catalyst. The reaction feed contains from 2–30 moles of steam for every mole of feed. Catalysts having higher potassium contents are usually employed at lower feed to steam ratios. Feed to steam ratios of from about 1:9 to about 1:18 are desirable. Good results are obtained with feed to steam ratios of about 1:12 to about 1:18.

The contact time of the reactant gas with the catalyst is usually defined in terms of gaseous-hourly-space velocity (volumes of hydrocarbon reactant per volume of catalyst per hour, i.e., GHSV). The GHSV according to this invention may vary from about 10 to 3,000 and is preferably adjusted within this range to effect the degree of conversion desired for the particular feed in question.

The preparation of catalysts, according to the invention, and their use will be further described by the following illustrative embodiments which are provided for illustration and are not to be construed as limiting the invention. It should be noted that advantages resulting from increases of selectivity of only one of two percentage points are extremely significant in a commercial process which may produce many hundreds of thousand pounds of product a day.

ILLUSTRATIVE EMBODIMENTS

Catalysts in accord with this invention were prepared by dry-blending molybdenum trioxide, cerous carbonate, cobaltous carbonate, vanadium pentoxide, potassium carbonate, chromium oxide with red iron oxide having a surface area of about 5m²/gm and an average particle size of 1 micron. Water containing dissolved therein sufficient potassium carbonate to give the desired final concentration is then added and the mixture is mulled and pelleted. The pellets were dried at 200° C. for 1/3 of an hour and then calcined at about 815° C. for about 60 minutes. This catalyst is denoted as Example I in Table I which gives the resultant composition. This catalyst was tested for activity and selectivity in the dehydrogenation of ethylbenzene to styrene by placing the catalyst pellets in a fixed reactor having a volume of 100 cc and passing a preheated mixture of steam and ethylbenzene at a molar ratio of 12:1 into the catalyst bed which was maintained at the temperature needed to effect the desired conversion of ethylbenzene. This temperature is dependent upon the activity of the catalyst. A pressure of about 0 to 1.5 inches of water was used and the liquid hourly space velocity of ethylbenzene was varied from about 0.65 to about $1.8h^{-1}$. The condensed liquid products were analyzed for styrene, ethylbenzene, benzene and toluene. These results were converted to activity and selectivity and are recorded in Table 1. The results for catalysts in accord with this invention prepared as above with differing concentrations of components are given in Table I. Tables III–VIII give the results of variations in concentrations of various catalyst components. Table II gives for comparison purposes the results for catalysts not according to this invention but which were prepared is a similar manner to that above. Table IX gives the results for a tungsten containing catalyst prepared as above, using ammonium metatungstate in place of the molybdenum trioxide.

In the following tables $T_{(70)}$ is used to represent the temperature in ° C. required to achieve 70 percent conversion, and $S_{(70)}$ is used to represent the selectivity at 70 percent conversion. $T_{(70)}$ is the indicium of activity, the higher the temperature, the lower the activity. The concentrations of the catalyst components are listed under the oxides in the tables in weight percents. The balance of the composition from those components listed is iron oxide.

TABLE I

| | IRON-BASED DEHYDROGENATION CATALYST PERFORMANCE | | | | | | | |
|---|---|---|---|---|---|---|---|---|
| Example | $K_2O$ | $V_2O_5$ | $MoO_3$ | $Ce_2O_3$ | $CoO$ | $Cr_2O_3$ | $T_{(70)}$ | $S_{(70)}$ |
| I-1 (avg) | 12.6 | 3.0 | 2.4 | 5.9 | 1.2 | 2.4 | 610 | 93.8 |
| I-2 | 12.6 | 4.5 | 3.6 | 11.9 | 1.8 | 2.4 | 618 | 92.5 |
| I-3 | 12.6 | 2.2 | 1.8 | 4.4 | 0.99 | 2.4 | 606 | 94.1 |
| I-4 | 12.6 | 1.5 | 1.2 | 8.0 | 0.63 | 2.4 | 604 | 94.3 |
| I-5 (avg) | 12.6 | 1.5 | 1.2 | 2.7 | 0.63 | 2.4 | 608 | 94.0 |
| I-6 | 12.6 | 0.75 | 0.6 | 1.4 | 0.36 | 2.4 | 609 | 93.6 |
| I-7 | 12.6 | 1.5 | 1.2 | 5.9 | 1.2 | 1.2 | 605 | 93.5 |
| I-8 | 12.6 | 0.5 | 0.5 | 5.9 | 1.2 | 0.5 | 607 | 93.3 |
| I-9 | 12.6 | 1.5 | 1.2 | 3.0 | 0.3 | 1.2 | 605 | 95.0 |
| I-10 | 12.6 | 1.5 | 1.2 | 3.0 | 0.3 | 1.2 | 611 | 94.8 |
| I-11 | 12.6 | 0.18 | 0.15 | 0.37 | 0.08 | 2.4 | 623 | 88.8 |
| I-12 | 12.6 | 0.37 | 0.30 | 0.75 | 0.15 | 0.30 | 623 | 92.5 |
| I-13 | 12.6 | 0.75 | 0.60 | 1.5 | 0.30 | 0.61 | 614 | 93.7 |
| I-14 | 12.6 | 1.5 | 1.2 | 3.0 | 0.60 | 1.2 | 604 | 94.4 |
| I-15 | 12.6 | 5.4 | 4.3 | 10.7 | 2.2 | 4.4. | 619 | 92.0 |
| I-16 | 12.6 | 5.7 | 4.6 | 11.3 | 2.3 | 2.5 | 622 | 94.0 |
| I-17 | 12.6 | 6.0 | 4.8 | 11.9 | 2.4 | 2.5 | ~650 | ~91 |
| I-18 | 12.6 | 9.0 | 7.2 | 17.8 | 3.6 | 2.5 | ~685 | ~90 |
| I-19 | 12.6 | 1.5 | 1.2 | 3.0 | 0 | 1.2 | 609 | 93.0 |
| I-20 | 12.6 | 1.5 | 1.2 | 3.0 | 0 | 1.2 | 612 | 94.5 |
| I-21 | 12.6 | 1.5 | 1.2 | 3.0 | 0 | 1.2 | 617 | 94.5 |
| I-22 | 12.6 | 1.5 | 1.2 | 3.0 | 0 | 1.2 | 614 | 94.5 |
| I-23 | 12.6 | 1.5 | 1.2 | 3.0 | 0 | 1.2 | 622 | 94.0 |
| I-24 | 12.6 | 1.5 | 1.2 | 3.0 | 0 | 0 | 613 | 95.0 |
| I-25 | 12.6 | 3.0 | 2.4 | 5.9 | 0 | 0 | 619 | 94.0 |
| I-26 | 12.6 | 3.0 | 2.4 | 5.9 | 1.2 | 0 | 610 | 94.0 |

TABLE II

| | IRON-BASED DEHYDROGENATION CATALYST PERFORMANCE | | | | | | | |
|---|---|---|---|---|---|---|---|---|
| Example | $K_2O$ | $V_2O_5$ | $MoO_3$ | $Ce_2O_3$ | $CoO$ | $Cr_2O_3$ | $T_{(70)}$ | $S_{(70)}$ |
| II-1 | 12.6 | 0 | 2.4 | 5.9 | 1.2 | 2.4 | 589 | 88.1 |
| II-2 | 12.6 | 0 | 0 | 5.9 | 1.6 | 2.4 | 590 | 86.6 |
| II-3 | 12.6 | 0 | 0 | 0 | 1.6 | 2.4 | 591 | 87.2 |
| II-4 | 12.6 | 0 | 0 | 0 | 0 | 2.4 | 592 | 86.4 |
| II-5 | 12.6 | 0 | 2.4 | 0 | 1.2 | 2.4 | 598 | 89.1 |
| II-6 | 12.6 | 0 | 2.4 | 5.9 | 0 | 2.4 | 598 | 89.4 |
| II-7 | 12.6 | 0 | 2.4 | 5.9 | 1.2 | 0 | 589 | 90.0 |
| II-8 | 12.6 | 0 | 2.4 | 5.9 | 0 | 0 | 605 | 89.5 |
| II-9 | 12.6 | 0 | 0 | 5.9 | 0 | 2.4 | 589 | 87.5 |
| II-10 | 12.6 | 0 | 2.4 | 0 | 1.2 | 0 | 611 | 89.5 |
| II-11* | 12.6 | 0 | 2.4 | 5.9 | 0 | 0 | 606 | 90.8 |
| II-12* | 12.6 | 3.0 | 0 | 0 | 1.2 | 2.4 | 608 | 91.5 |
| II-13* | 12.6 | 3.0 | 0 | 0 | 1.2 | 0 | 624 | 92.0 |
| II-14* | 12.6 | 3.0 | 0 | 5.9 | 0 | 0 | 604 | 92.5 |
| II-15* | 12.6 | 3.0 | 2.4 | 0 | 1.2 | 0 | >640 | — |
| II-16 | 12.6 | 0 | 0 | 5.9 | 0 | 0 | 584 | 87.9 |

*Calcined for 4 hours at 950° F and then for 4 hours at 1400° F.

TABLE III

EFFECT OF POTASSIUM ON IRON-BASED DEHYDROGENATION CATALYST

| Example | $K_2O$ | $V_2O_5$ | $MoO_3$ | $Ce_2O_3$ | CoO | $Cr_2O_3$ | $T_{(70)}$ | $S_{(70)}$ |
|---|---|---|---|---|---|---|---|---|
| III-1 | 5.0 | 1.5 | 1.2 | 3.0 | 0.30 | 1.2 | ~620* | ~92 |
| III-2 | 9.6 | 1.5 | 1.2 | 3.0 | 0.63 | 2.4 | 610 | 93.6 |
| III-3 | 10.6 | 1.5 | 1.2 | 3.0 | 0.30 | 1.2 | 607 | 93.6 |
| III-4 | 12.6 | 1.5 | 1.2 | 3.0 | 0.30 | 1.2 | 611 | 94.8 |
| III-5 | 12.6 | 1.5 | 1.2 | 3.0 | 0.63 | 2.4 | 604 | 94.2 |
| III-6 | 12.6 | 1.5 | 1.2 | 3.0 | 0.63 | 2.4 | 608 | 93.8 |
| III-7 | 14.6 | 1.5 | 1.2 | 3.0 | 0.30 | 2.4 | 608 | 93.4 |
| III-8 | 16.6 | 1.5 | 1.2 | 3.0 | 0.63 | 2.4 | 618 | 93.9 |

*Losing activity

TABLE IV

EFFECT OF VANADIUM VARIATION ON IRON-BASED DEHYDROGENATION CATALYSTS

| Example | $K_2O$ | $V_2O_5$ | $MoO_3$ | $Ce_2O_3$ | CoO | $Cr_2O_3$ | $T_{(70)}$ | $S_{(70)}$ |
|---|---|---|---|---|---|---|---|---|
| IV-1 | *12.6 | 0 | 2.4 | 5.9 | 1.2 | 2.4 | 595 | 89.3 |
| IV-2 | *12.6 | 3.0 | 2.4 | 5.9 | 1.2 | 2.4 | 610 | 93.5 |
| IV-3 | 12.6 | 0 | 2.4 | 5.9 | 1.2 | 2.4 | 589 | 88.1 |
| IV-4 | 12.6 | 3.0 | 2.4 | 5.9 | 1.2 | 2.4 | 613 | 93.8 |
| IV-5 | 12.6 | 0 | 2.4 | 5.9 | 1.2 | 0 | 589 | 90.1 |
| IV-6 | 12.6 | 3.0 | 2.4 | 5.9 | 1.2 | 0 | 608 | 94.4 |
| IV-7 | 12.6 | 0.5 | 2.4 | 5.9 | 1.2 | 2.4 | 605 | 91.5 |
| IV-8 | 12.6 | 0.75 | 2.4 | 5.9 | 1.2 | 2.4 | 608 | 93.3 |
| IV-9 | 12.6 | 6.0 | 2.4 | 5.9 | 1.2 | 2.4 | 632 | 92.1 |
| IV-10 | 12.6 | 9.0 | 2.4 | 5.9 | 1.2 | 2.4 | 652 | 88.0 |
| IV-11 | 12.6 | 0.75 | 1.2 | 3.0 | 0.3 | 1.2 | 610 | 92.8 |
| IV-12 | 12.6 | 1.5 | 1.2 | 3.0 | 0.3 | 1.2 | 611 | 94.8 |
| IV-13 | 12.6 | 2.2 | 1.2 | 3.0 | 0.3 | 1.2 | 616 | 94.7 |
| IV-14 | 12.6 | 2.2 | 1.2 | 3.0 | 0.3 | 1.2 | 606 | 94.2 |
| IV-15 | 12.6 | 3.0 | 1.2 | 3.0 | 0.3 | 1.2 | 604 | 94.7 |
| IV-16 | 12.6 | 6.0 | 1.2 | 3.0 | 0.3 | 1.2 | 619 | 93.5 |
| IV-17 | 12.6 | 12.0 | 2.2 | 9.7 | 2.2 | 2.4 | ~700 | <88 |

*Calcined for 4 hours at 950° F and then for 4 hours at 1400° F.

TABLE V

EFFECT OF MOLYBDENUM ON IRON-BASED DEHYDROGENATION CATALYSTS

| Example | $K_2O$ | $V_2O_5$ | $MoO_3$ | $Ce_2O_3$ | CoO | $Cr_2O_3$ | $T_{(70)}$ | $S_{(70)}$ |
|---|---|---|---|---|---|---|---|---|
| V-1 | *12.6 | 1.5 | 0 | 3.0 | 0.30 | 1.2 | 603 | 92.5 |
| V-2 | *12.6 | 1.5 | 0.6 | 3.0 | 0.30 | 1.2 | 615 | 94.0 |
| V-3 | 12.6 | 1.5 | 1.8 | 3.0 | 0.30 | 1.2 | 619 | 93.0 |
| V-4 | 12.6 | 1.5 | 0 | 3.0 | 0.63 | 2.4 | 611 | 91.8 |
| V-5 | 12.6 | 1.5 | 0.5 | 3.0 | 0.63 | 2.4 | 620 | 92.8 |
| V-6 (Avg) | 12.6 | 1.5 | 1.2 | 3.0 | 0.63 | 2.4 | 608 | 94.0 |
| V-7 | 12.6 | 3.0 | 0 | 5.9 | 1.2 | 2.4 | 604 | 92.5 |
| V-8 | 12.6 | 3.0 | 0.6 | 5.9 | 1.2 | 2.4 | 613 | 91.2 |
| V-9 | 12.6 | 3.0 | 1.0 | 5.9 | 1.2 | 2.4 | 613 | 93.8 |
| V-10 | 12.6 | 3.0 | 2.4 | 5.9 | 1.2 | 2.4 | 607 | 94.0 |
| V-11 | 12.6 | 3.0 | 2.4 | 5.9 | 1.2 | 2.4 | 611 | 93.7 |
| V-12 | 12.6 | 3.0 | 4.7 | 5.9 | 1.2 | 2.4 | 620 | 92.5 |
| V-13 | 12.6 | 3.0 | 8.0 | 5.9 | 1.2 | 2.4 | 628 | 93.8 |
| V-14 | 12.6 | 3.0 | 9.0 | 5.9 | 1.2 | 2.4 | 652 | ~88 |

*Calcined for 50 minutes at up to 930° C.

TABLE VI

EFFECT OF CERIUM ON IRON-BASED DEHYDROGENATING CATAYSTS

| Example | $K_2O$ | $V_2O_5$ | $MoO_3$ | $Ce_2O_3$ | CoO | $Cr_2O_3$ | $T_{(70)}$ | $S_{(70)}$ |
|---|---|---|---|---|---|---|---|---|
| VI-1 | 12.6 | 1.5 | 1.2 | 2.2 | 0.3 | 1.2 | 622 | 93.4 |
| VI-2 | 12.6 | 1.5 | 1.2 | 3.7 | 0.3 | 1.2 | 610 | 93.6 |
| VI-3 | *12.6 | 3.0 | 2.4 | 0 | 1.2 | 2.4 | 650 | 89.8 |
| VI-4 | 12.6 | 3.0 | 2.4 | 1.5 | 1.2 | 2.4 | 620 | 91.4 |
| VI-5 | 12.6 | 3.0 | 2.4 | 5.9 | 1.2 | 2.4 | 606 | 94.0 |
| VI-6 | 12.6 | 3.0 | 2.4 | 5.9 | 1.2 | 2.4 | 611 | 93.7 |
| VI-7 | 12.6 | 3.0 | 2.4 | 11.9 | 1.2 | 2.4 | 611 | 92.4 |
| VI-8 | 12.6 | 3.0 | 2.4 | 11.9 | 1.2 | 2.4 | 616 | 93.4 |
| VI-9 | 12.6 | 3.0 | 2.4 | 19.2 | 1.2 | 2.4 | 613 | 92.5 |
| VI-10 | 12.6 | 3.0 | 2.4 | 38.5 | 1.2 | 2.4 | 617 | 92.5 |
| VI-11 | 12.6 | 3.0 | 2.4 | 77.0 | 1.2 | 2.4 | ~630** | ~92 |

*Calcined for 4 hours at 950° F and then for 4 hours at 1500° F
**Losing activity

TABLE VII

EFFECT OF COBALT ON IRON-BASED DEHYDROGENATION CATALYSTS

| Example | $K_2O$ | $V_2O_5$ | $MoO_3$ | $Ce_2O_3$ | CoO | $Cr_2O_3$ | $T_{(70)}$ | $S_{(70)}$ |
|---|---|---|---|---|---|---|---|---|
| VII-1 | 12.6 | 1.5 | 1.2 | 3.0 | 0 | 1.2 | 609 | 93.0 |
| VII-2 | 12.6 | 1.5 | 1.2 | 3.0 | 15.0 | 2.4 | 618 | 92.5 |

TABLE VII-continued
EFFECT OF COBALT ON IRON-BASED DEHYDROGENATION CATALYSTS

| Example | K$_2$O | V$_2$O$_5$ | MoO$_3$ | Ce$_2$O$_3$ | CoO | Cr$_2$O$_3$ | T$_{(70)}$ | S$_{(70)}$ |
|---|---|---|---|---|---|---|---|---|
| VII-3 | 12.6 | 1.5 | 1.2 | 3.0 | 30.0 | 2.4 | 622 | 94.0 |
| VII-4 | 12.6 | 1.5 | 1.2 | 3.0 | 40.0 | 1.2 | 630 | 93.1 |
| VII-5 | 12.6 | 1.5 | 1.2 | 3.0 | 50.0 | 1.2 | 629** | 94.6 |
| VII-6* | 12.6 | 3.0 | 2.4 | 5.9 | 0 | 2.4 | 618 | 93.5 |
| VII-7 | 12.6 | 3.0 | 2.4 | 5.9 | 0.3 | 2.4 | 605 | 93.8 |
| VII-8 | 12.6 | 3.0 | 2.4 | 5.9 | 5.0 | 2.4 | 612 | 92.5 |
| VII-9 | 12.6 | 3.0 | 2.4 | 5.9 | 12.0 | 2.4 | 608 | 93.8 |
| VII-10 | 12.6 | 3.0 | 2.4 | 5.9 | 30.0 | 2.4 | 628 | 94.0 |

*Calcined for 4 hours at 950° F and then for 4 hours at 1500° F.
**Losing activity

TABLE VIII
EFFECT OF CHROMIUM ON IRON-BASED DEHYDROGENATION CATALYSTS

| Example | K$_2$O | V$_2$O$_5$ | MoO$_3$ | Ce$_2$O$_3$ | CoO | Cr$_2$O$_3$ | T$_{(70)}$ | S$_{(70)}$ |
|---|---|---|---|---|---|---|---|---|
| VIII-1 | 9.6 | 1.5 | 1.2 | 3.0 | 0.63 | 0 | 610 | 95.0 |
| VIII-2 | 12.6 | 1.5 | 2.4 | 5.9 | 0.6 | 0 | 619 | 94.5 |
| VIII-3 | 12.6 | 3.0 | 2.4 | 5.9 | 1.2 | 0 | 608 | 94.4 |
| VIII-4 | 12.6 | 1.5 | 1.2 | 3.0 | 0.3 | 0.6 | 609 | 94.7 |
| VIII-5 | 12.6 | 1.5 | 1.2 | 3.0 | 0.2 | 1.2 | 611 | 94.8 |
| VIII-6 | 12.6 | 3.0 | 2.4 | 5.9 | 1.2 | 4.9 | 612 | 92.9 |
| VIII-7 | 12.6 | 3.0 | 2.4 | 5.9 | 1.2 | 7.4 | 617 | 91.0 |
| VIII-8 | 12.6 | 3.0 | 2.4 | 5.9 | 1.2 | 10.0 | 618 | 93.0 |
| VIII-9 | 12.6 | 3.0 | 2.4 | 5.9 | 1.2 | 20.0 | 632 | 93.0 |

TABLE IX
TUNGSTEN-CONTAINING IRON-BASED DEHYDROGENATION CATALYST

| K$_2$O | V$_2$O$_5$ | WO$_3$ | Ce$_2$O$_3$ | CoO | Cr$_2$O$_3$ | T$_{(70)}$ | S$_{(70)}$ |
|---|---|---|---|---|---|---|---|
| 12.6 | 3.0 | 2.3 | 2.7 | 0.3 | 1.2 | 609 | 94.6 |

What is claimed is:

1. A catalyst for the dehydrogenation of hydrocarbons to more unsaturated hydrocarbons comprising a mixture having:
   (a) from about 14 to about 67 percent by weight of an iron oxide, measured as iron metal;
   (b) from about 2 to about 25 percent by weight of potassium oxide, measured as potassium metal;
   (c) from about 0.005 to about 5 percent by weight of a vanadium oxide, measured as vanadium metal;
   (d) from about 0.006 to about 16 percent by weight of a heavy metal oxide selected from the group consisting of molybdenum oxide, tungsten oxide and mixtures thereof, measured as the metal;
   (e) from about 0.008 to about 43 percent by weight of a cerium oxide, measured as cerium metal;
   (f) from 0 to about 40 percent by weight of a cobalt oxide measured as cobalt metal; and
   (g) from 0 to about 21 percent by weight of a chromium oxide, measured as chromium metal.

2. The catalyst of claim 1 wherein:
   (a) the iron oxide ranges from about 17 to about 63 percent by weight;
   (b) the potassium oxide ranges from about 4 to about 21 percent by weight;
   (c) the vanadium oxide ranges from about 0.05 to about 5 percent by weight;
   (d) the heavy metal oxide ranges from about 0.06 to about 16 percent by weight;
   (e) the cerium oxide ranges from about 0.08 to about 26 percent by weight;
   (f) the cobalt oxide ranges from 0 to about 32 percent by weight; and
   (g) the chromium oxide ranges from 0 to about 14 percent by weight.

3. The catalyst of claim 1 wherein the hydrocarbon is a monoolefin, the more unsaturated hydrocarbon is a diene, the iron oxide ranges from about 21 to about 53 percent by weight, and the potassium oxide ranges from about 12 to about 25 percent by weight.

4. The catalyst of claim 3 wherein the mono-olefin is butylene and the diene is butadiene.

5. The catalyst of claim 1 wherein the hydrocarbon is an alkyl aromatic hydrocarbon, and the more unsaturated hydrocarbon is an alkenyl aromatic hydrocarbon, the iron oxide ranges from about 27 to about 63 percent by weight, and the potassium oxide ranges from about 4 to about 17 percent by weight.

6. The catalyst of claim 5 wherein the hydrocarbon is ethylbenzene and the more unsaturated hydrocarbon is styrene and wherein the vanadium oxide ranges from about 0.05 to about 5 percent by weight, the heavy metal oxide ranges from about 0.06 to about 12 percent by weight, the cerium oxide ranges from about 0.08 to about 26 percent by weight; the cobalt oxide ranges from 0 to about 32 percent by weight and the chromium oxide ranges from 0 to about 14 percent by weight.

7. The catalyst of claim 6 wherein the vanadium oxide ranges from about 0.1 to about 4 percent by weight, the heavy metal oxide ranges from about 0.2 to about 8 percent by weight, the cerium oxide ranges from about 0.2 to about 17 percent by weight, the cobalt ranges from 0 to about 24 percent by weight, and the chromium ranges from 0 to about 14 percent by weight.

8. The process for preparing the catalyst of claim 1 wherein iron, potassium, vanadium, molybdenum and/or tungsten, cerium, cobalt (when present) and chromium (when present) oxides and/or compounds thermally decomposable to oxides upon calcination are combined with water to form a paste, the paste is formed into pellets, the pellets are dried and then calcined at a temperature ranging from about 600° C. to about 1000° C.

9. The process of claim 8 wherein the drying and calcining are performed sequentially in one step.

10. The process for preparing the catalyst of claim 6 wherein iron, potassium, vanadium, molybdenum and/or tungsten, cerium, cobalt (when present) and chromium (when present) oxides and/or compounds thermally decomposable to oxides upon calcination are combined with water to form a paste, the paste is formed into pellets, the pellets are dried and then calcined at a temperature ranging from about 600° C. to about 1000° C.

11. The process of claim 10 wherein the drying and calcining are performed sequentially in one step.

* * * * *